United States Patent [19]

Baier et al.

[11] Patent Number: 4,623,593

[45] Date of Patent: Nov. 18, 1986

[54] SELF-ADHESIVE POLYMER COMPOSITION FOR USE AS PROSTHETIC APPLIANCE

[75] Inventors: Robert E. Baier, Amherst, N.Y.; Keith Kent, c/o Calspan Corporation, 4455 Genesee St., Buffalo, N.Y. 14225

[73] Assignee: Keith Kent, Tampa, Fla.

[21] Appl. No.: 512,872

[22] Filed: Jul. 12, 1983

[51] Int. Cl.$^4$ .................. B32B 9/04; C08G 77/06; B29B 7/36

[52] U.S. Cl. .................. 428/447; 264/45.5; 264/338; 264/DIG. 18; 428/318.8; 428/343; 428/346; 428/355; 428/356; 428/423.4; 528/17; 525/937

[58] Field of Search .............. 428/318.8, 355, 356, 428/343, 346; 525/937

[56] References Cited

U.S. PATENT DOCUMENTS

| | | | |
|---|---|---|---|
| 3,059,764 | 10/1962 | Tomita et al. | 428/346 |
| 3,251,910 | 5/1966 | Barnhart | 264/17 |
| 3,258,509 | 6/1966 | Barnhart | 264/17 |
| 3,288,893 | 11/1966 | Stebleton | 264/17 |
| 3,475,363 | 10/1969 | Gander | 428/343 |
| 3,607,977 | 9/1971 | Taylor et al. | 260/876 |
| 3,681,786 | 8/1972 | Lynch | 3/1 |
| 3,732,122 | 5/1973 | Fehrn-Christensen | 428/343 |
| 3,762,978 | 10/1973 | Holmes et al. | 156/308 |
| 3,813,364 | 5/1974 | Zuba et al. | 260/375 B |
| 3,961,379 | 6/1976 | Highgate | 3/13 |
| 4,251,302 | 2/1981 | Leonard et al. | 156/60 |
| 4,332,844 | 6/1982 | Hamada et al. | 427/387 |

OTHER PUBLICATIONS

Buist, Developments in Polyurethane-1, Applied Science Publishers Ltd., London, (1978), p. 90.

Primary Examiner—Herbert S. Cockeram
Attorney, Agent, or Firm—Herbert L. Bello

[57] ABSTRACT

Polymer compositions and methods of making them are provided. Selected surface layers of the polymers, integral with the polymer body, possess pressure sensitive adhesive properties. The polymers are cured with the selected surfaces in contact with a cross-linking inhibition agent which controls the amount of cross-linking of the polymer taking place at the surface. The polymers are useful as, or in conjunction with, prosthetic appliances which are adhered to skin or other substrates.

3 Claims, No Drawings

SELF-ADHESIVE POLYMER COMPOSITION FOR USE AS PROSTHETIC APPLIANCE

BACKGROUND OF THE INVENTION

This invention relates to polymeric compositions and their preparation, which compositions when cured have an integral permanently tacky surface layer, and more particularly to self-adhering polymers used as prosthetic appliances.

Our society places a heavy emphasis on physical attributes. Because of this, a person with a congenital, developmental, or acquired defect may be considered by some as socially unacceptable subconsciously, if not overtly. Such defects also affect a person's self-image. Since facial appearance and expression are both highly visible and a primary means of communication, defects of the head and neck areas are more socially traumatic than defects of other body parts. The preparation of maxillofacial prosthetics requires the use of both art and science in reconstructing defects using polymeric synthetic materials The goal of maxillofacial prosthetics is establishing function, fit, appearance, and physiology.

There are two general categories of maxillofacial prosthetics, namely, intraoral and extraoral. Intraoral prostheses are usually fabricated in association with a partial or complete denture. Retention of intraoral prostheses usually pose few problems except in a completely edentulous patient having markedly resorbed ridges, poor quality bony or soft tissue undercuts, and a bulky or weighty obturator. Extraoral prostheses pose more retentive as well as aesthetic problems. A major problem for a patient wearing an extraoral prosthetic device is the potential for dislodgement, and concomitant patient embarassment during normal activity.

A number of different types of polymeric materials have been utilized as base materials for prostheses. Principal among these polymers have been the silicone rubbers and polyurethanes. These elastomeric polymers are used for most extraoral prostheses because of the life-like qualities that can be imparted to them. These qualities include flexibility and the ability to be colored. This coloring is accomplished by adding fibers or pigment to the prepolymer or by tattooing the completed prostheses to conform them closely to the skin tones of the areas contiguous to the reconstructive site.

The chemical inertness of these polymers once cured is a major factor in their popularity in maxillofacial prosthetic reconstruction. However, the same chemical inertness and inherently non-stick properties which makes polymers such as silicone rubbers desirable prosthetic materials also is the cause of the majority of difficulties in working with them. While in some cases the use of surgery to provide tissue undercuts to aid in mechanically retaining a prosthesis is possible, in many other cases adhesives alone, or in combination with other mechanical retention aids such as wires, elastics, or eyeglasses, must be used as the primary means for retention. For example, a prosthetic ear may have virtually no other means for retention than an adhesive. This is also true in most cases where the defect is large or cannot be surgically modified to provide mechanical retention.

At the present time, we know of no completely satisfactory and medically safe adhesive for routinely securing, and regularly detaching for hygienic purposes, prosthetic devices. The problems of applying adhesives to and retaining them on inherently non-stick surfaces, such as silicone rubber, are readily apparent. These problems are compounded by the presence of surface contaminants such as dirt, oils, and dead skin on the tissue to which the prosthetic device is to be applied. Once cured, many adhesives no longer are sticky and will not bond again after removal. Also, many adhesives that have pressure sensitive properties lose their adherent properties once their surface has been contaminated.

Accordingly, the need exists in the art for medically acceptable polymer compositions suitable for use as prosthetic devices which possess permanently adherent, properties and which can be repetitively applied and detached from human skin or other surfaces.

SUMMARY OF THE INVENTION

The present invention meets this need by providing polymer compositions, and methods for their preparation, with integral surface layers having permanently tacky, pressure sensitive adhesive properties and which are suitable for use as prosthetic appliances. Many polymeric materials are useful in the practice of the present invention, with preferred polymers being those which are cured or vulcanized by a crosslinking reaction of monomeric, prepolymeric, or unvulcanized polymeric components and mixtures thereof. Most preferred for use as prosthetic appliances are so-called "medical grade" compositions which are physiologically inert.

We have found that an integral surface layer having pressure-sensitive adhesive properties may be formed on an otherwise fully cured polymeric body. This may be accomplished by applying a sufficient amount of a cross-linking inhibition agent to selected surfaces of a mold cavity prior to packing the cavity with uncured monomeric, prepolymeric, or unvulcanized polymeric material. The mold is then closed and the material cured. The cross-linking inhibition agent acts on the surface or surfaces of the polymer to prevent complete cross-linking thereof. The body of the polymer is otherwise completely cured and has the same properties as would be expected. Conventional additives such as fibers and fillers may be added to the uncured compound and have no effect on the integral surface layer which is formed.

However, the surface or surfaces of the polymeric body which were cured in contact with the cross-linking inhibition agent remain tacky and possess pressure sensitive adhesive properties. We believe that these pressure sensitive adhesive properties result from the absence of complete cross-linking of the surface layer of the polymeric body. Thus, the surface of the body presents a multiplicity of elastomeric "fingers" or "hairs" which are an integral part of an otherwise completely cured polymeric body. We believe that it is the multiplicity of "fingers" or "hairs" and their chemical nature which, when placed in contact with a substrate, cause the polymeric body to adhere to the substrate.

The polymeric composition of the present invention has particular utility when used as a prosthetic appliance for attachment to human skin. The appliance can be repetitively applied and detached from skin, or other surfaces, without loss of effectiveness of its adhesive properties. Because the adhesive surface layer is integral with the body of the appliance, little or no adhesive will debond or leave a residue on the skin or other surface. Additionally, simple washing of the adhesive surface layer with soapy water or solvents such as acetone or alcohol will effectively remove any built-up contaminant layers of oils, greases, dirt, or undesirable biota. After drying, the original adhesive quality of the surface will be restored.

Accordingly, it is an object of the present invention to provide a polymeric composition having an integral surface layer with pressure sensitive adhesive properties useful in prosthetic appliances. This and other objects and advantages of the invention will become apparent from the following detailed description and the appended claims.

DESCRIPTION OF THE PREFERRED EMBODIMENTS

Many polymeric materials may be applicable in the practice of the present invention. Examples of polymers previously used in or as prosthetic appliances include acrylics, polyurethanes, silicones, polyesters, polyolefins, polyacrylamides, and polyether-urethane copolymers. Other suitable, medically acceptable polymers are also well known to those skilled in the art. We have found that the surface of a polymeric material can be modified by the practice of the present invention to give that surface pressure sensitive adhesive properties even though the remainder of the body of the polymer exhibits no adhesive properties and may, in fact, exhibit so-called "nonstick" properties. Silicone rubbers are a prime example of this. The polymers presently preferred in the practice of the present invention are silicone elastomers and specifically polydimethylsiloxanes because of their ready availability and acceptance for medical applications.

Without wishing to be limited to any specific theory or mechanism, we believe that the application of certain agents, which we will term cross-linking inhibition agents, to one or more selected surfaces of a mold cavity will inhibit the degree of cross-linking which occurs on the surface of the polymeric composition during a curing or vulcanization step. This results in a surface layer which presents a multiplicity of elastomeric polymer chains which at one end are integral with the body of the otherwise fully cured polymer but at the other end are free. We have found several suitable cross-linking inhibition agents including cyanoacrylate polymers and metal salts of carboxylic acids such as stannous octoate. Those skilled in the art may determine other suitable cross-linking inhibition agents by simple testing.

The polymer compositions of the present invention are preferably cured or vulcanized in a mold to form a variety of shapes and prosthetic appliances. A preferred material for the mold is dental stone, although other mold materials such as metals or the like may be used. After fabrication of the mold, the cross-linking inhibition agent is applied to one or more selected surfaces of the mold cavity, namely those surfaces which correspond to surfaces on the finished polymer or prosthetic appliance for which a pressure-sensitive adhesive surface layer is desired. The cross-linking inhibition agent may be applied by any suitable means such as brushing or spraying and allowed to dry. In many instances, the ease of application of the cross-linking inhibition agent may be enhanced by the use of a solvent such as acetone or alcohol. The amount of cross-linking inhibition agent applied will affect the depth of the surface layer having pressure sensitive adhesive properties which is formed. By modifying the amount of cross-linking inhibition applied to the surface of the mold cavity one can control the surface adhesive properties on the cured polymer.

After the cross-linking inhibition agent is dried, the monomeric, prepolymeric, or unvulcanized composition is packed into the mold cavity and the mold closed. Depending upon the particular composition utilized, vulcanization or curing is then carried out at temperatures and times sufficient for the body of the composition to cure completely. Curing times and temperatures for specific compositions are well-known to those skilled in the art. For example, if silicone rubber is being cured, it may be a room temperature vulcanizing rubber or one that requires the application of heat (e.g., 150°–250° F.). Conventional additives such as fibers or fillers may be premixed with the uncured composition.

After curing has been completed, the mold is allowed to cool (if necessary) and the finished composition or prosthetic appliance is removed. The surface or surfaces of the polymer body which were cured in contact with the cross-linking inhibition agent will exhibit pressure sensitive adhesive properties, whereas the body of the polymer will otherwise exhibit those properties (i.e., strength, tear resistance, etc.) which would be expected of a fully cured polymer.

The surface layer of the polymer retains its pressure sensitive adhesive properties for the life of the polymer and remains integrally attached thereto. The surface layer may be secured to human skin or other substrates and repeatedly detached and reattached. If the surface layer becomes contaminated with oils, dirt, or undesirable biota, it may be readily cleaned and restored to its original state after drying by washing it with soapy water, acetone, or other suitable cleaning agents.

In order that those skilled in the art can better understand how the present invention can be practised, the following nonlimiting examples are given by way of illustration.

EXAMPLE 1

A mold was fabricated using air mixed dental stone (commercially available under the designation of Denstone from Columbus Dental Manufacturing Co., Columbus, Ohio) and a water/powder ratio of 30 cc/100gm. Selected surfaces of the mold cavity were painted with a cross-linking inhibition agent comprising a mixture of stannous octoate and denatured alcohol (1:10 ratio) and allowed to air dry. The mold cavity was then packed with a catalyzed, deaerated silicone prepolymer designated MDX4-4210 and commercially available from Dow Corning Corp., Midland, Michigan. The silicone prepolymer is believed to be a polydimethylsiloxane based silicone elastomer. After the mold was closed, vulcanization was accelerated by heating the mold at 200°–220° F. for approximately 2 hours. After the mold was cooled, the resulting polymer body was removed.

The silicone rubber body exhibited the expected physical properties of a fully cured material except for those surfaces which had been cured in contact with the cross-linking inhibition agent. Those surfaces exhibited tack and pressure sensitive adhesive properties.

EXAMPLE 2

The surface of a dental stone mold (Denstone) was cleaned successively by application of soap and water, carbon tetrachloride, chloroform, and methanol and then air dried. A cyanoacrylate alpha-or iso-cyanoacrylate cross-linking inhibition agent was applied to selected surfaces of the mold and allowed to air dry. The mold cavity was then packed with a catalyzed, deaerated silicone prepolymer (MDX4-4210) and the mold closed. The silicone was vulcanized by heating the mold at 80° C. for 24 hours. After cooling, the polymer body was removed from the mold. The surfaces of the polymer which were cured in contact with the cross-linking inhibition agent were tacky and exhibited pressure sensitive adhesive properties.

The same experiment was run under the same conditions as above with the exception that the mold was packed with the silicone prepolymer before the cross-linking inhibition agent had dried. After 24 hours, the polymer had not cured indicating that the cyanoacrylate should be allowed to dry before the mold is packed.

EXAMPLE 3

The surface of a dental stone mold was cleaned as in Example 2 above and dried. A cyanoacrylate (alpha- or iso-cyanoacrylate) cross-linking inhibition agent was applied to selected surfaces of the mold and allowed to air dry. The dry cyanoacrylate was then coated with the catalyst for MDX4-4210 and the catalyst allowed to dry. The mold was then packed with catalyzed, deaerated MDX4-4210 silicone prepolymer and vulcanized as in Example 2. The resulting polymer surfaces which had cured in contact with the cross-linking inhibition agent and catalyst were tacky and exhibited pressure sensitive adhesive properties.

EXAMPLE 4

The procedure of Example 3 was repeated except that a stannous octoate catalyst was applied over the dried cyanoacrylate and the silicone prepolymer packed in the mold was GE RTV11 (commercially available from the General Electric Co.). Again, the surfaces of the polymer body which had cured in contact with the cross-linking inhibition agent and catalyst were tacky and exhibited pressure sensitive adhesive properties.

EXAMPLE 5

The procedure of Example 3 was repeated except that a stannous octoate catalyst was applied over the dried cyanoacrylate and the silicone prepolymer packed in the mold was Silastic 382 (commercially available from Dow Corning Corp.). Once again, the surfaces of the polymer body which had cured in contact with the cross-linking inhibition agent and catalyst were tacky and exhibited pressure sensitive adhesive properties.

What is claimed is:
1. An elastomeric polymeric article comprising:
   a cured, non-tacky base polymer having an integral surface layer,
   said surface layer of said base polymer being modified to have an inhibited, limited degree of crosslinking so that said surface layer has pressure sensitive adhesive properties, said polymer being a silicone rubber.
2. An elastomeric polymeric article comprising:
   a cured, non-tacky base polymer having an integral surface layer,
   said surface layer of said base polymer being modified to have an inhibited, limited degree of crosslinking so that said surface layer has pressure sensitive adhesive properties, said polymer being a polydimethylsiloxane.
3. An elastomeric polymeric article comprising:
   a cured, non-tacky base polymer selected from the group consisting of silicone and siloxane, said base polymer having an integral surface layer,
   said surface layer of said base polymer being modified to have an inhibited, limited degree of crosslinking so that said surface layer has pressure sensitive adhesive properties.

* * * * *